United States Patent [19]

Samuels

[11] Patent Number: 6,047,825
[45] Date of Patent: Apr. 11, 2000

[54] METHOD AND APPARATUS FOR STORING MEDICAL GUIDEWIRES

[76] Inventor: Shaun Lawrence Wilkie Samuels, 1055 Sonoma Ave., Menlo Park, Calif. 94025

[21] Appl. No.: 09/138,028

[22] Filed: Aug. 21, 1998

[51] Int. Cl.[7] .................................................. B65D 83/10
[52] U.S. Cl. ........................... 206/364; 206/804; 206/438
[58] Field of Search ................................... 206/363, 364, 206/370, 702, 804, 438, 63.3, 389, 315.6, 227, 225; 600/585; 220/554, 552

[56] References Cited

U.S. PATENT DOCUMENTS

| | | |
|---|---|---|
| 156,586 | 11/1874 | McNeill . |
| 539,654 | 5/1895 | Stewart . |
| 1,816,301 | 7/1931 | Sundell . |
| 1,926,836 | 9/1933 | Corlett . |
| 2,920,394 | 1/1960 | Soderbergh . |
| 3,902,679 | 9/1975 | Bost . |
| 5,575,382 | 11/1996 | Sobel et al. . |
| 5,609,311 | 3/1997 | Palm . |

*Primary Examiner*—David T. Fidei
*Assistant Examiner*—Nhan T. Lam
*Attorney, Agent, or Firm*—Piper Marbury Rudnick & Wolfe

[57] ABSTRACT

A flexible pipe features an open end and a closed end. A nozzle is attached by a friction joint to the open end and features an elbow portion so that it is maintained above the level of the flexible pipe. Alternatively, the open end of the flexible pipe is elevated by a collar or stand. As a result, fluid may be retained within the flexible pipe. The nozzle or open end of the flexible pipe is also flared and features dividers so that guidewires placed within the flexible pipe may be easily accessed by a physician. The flexible pipe may be held in a coiled configuration by clamps. Alternatively, the flexible pipe may be straightened out and attached to a surface, such as the sterile drapes covering a patient, by way of one or more wire/catheter guides. Each wire/catheter guide features one or more channels positioned on a base. The channels are sized to grip the flexible pipe and the bottom of the base is provided with adhesive so the wire/catheter guide may be attached to the surface of interest.

20 Claims, 3 Drawing Sheets

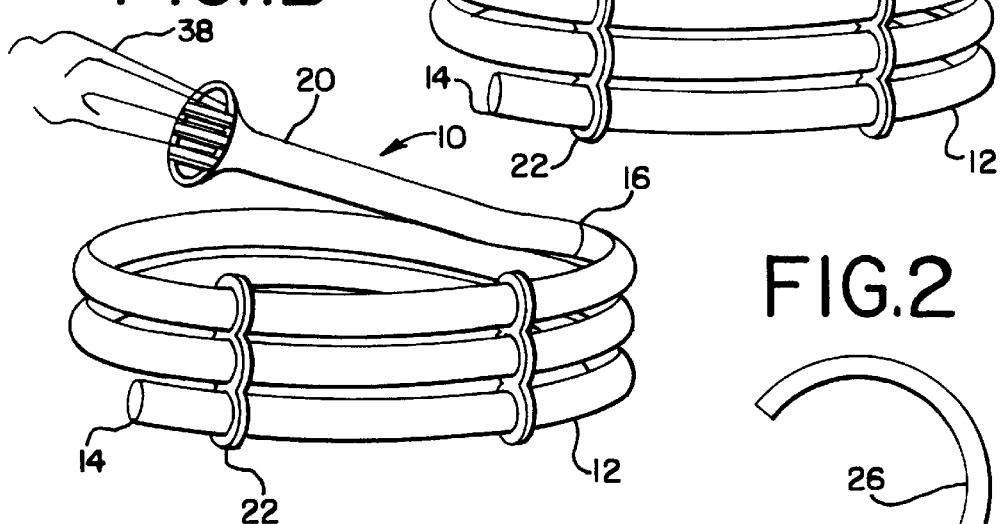
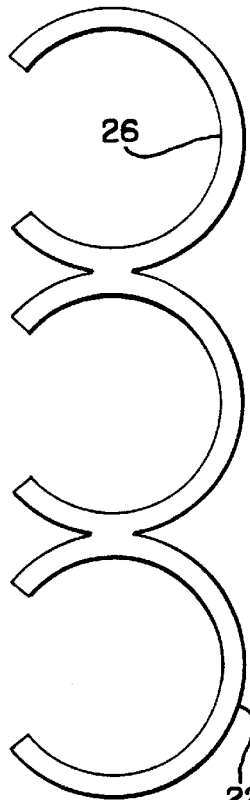
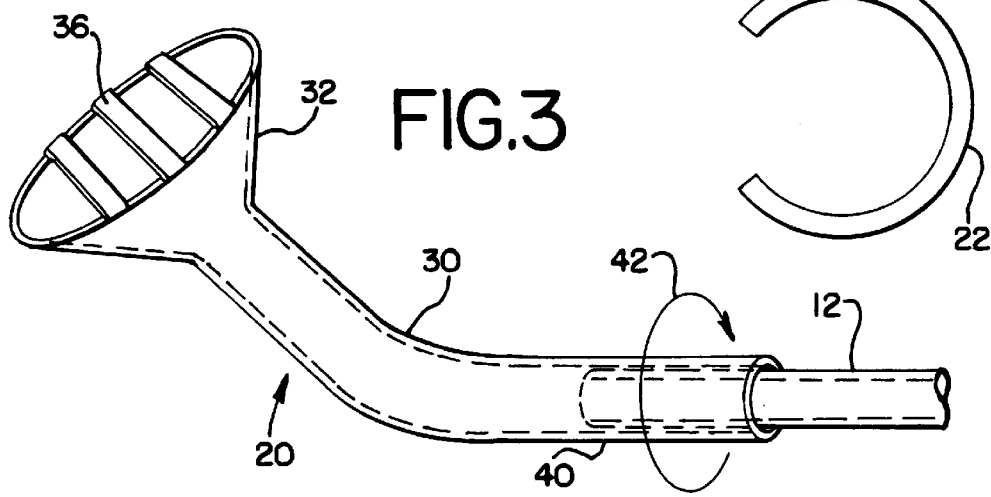

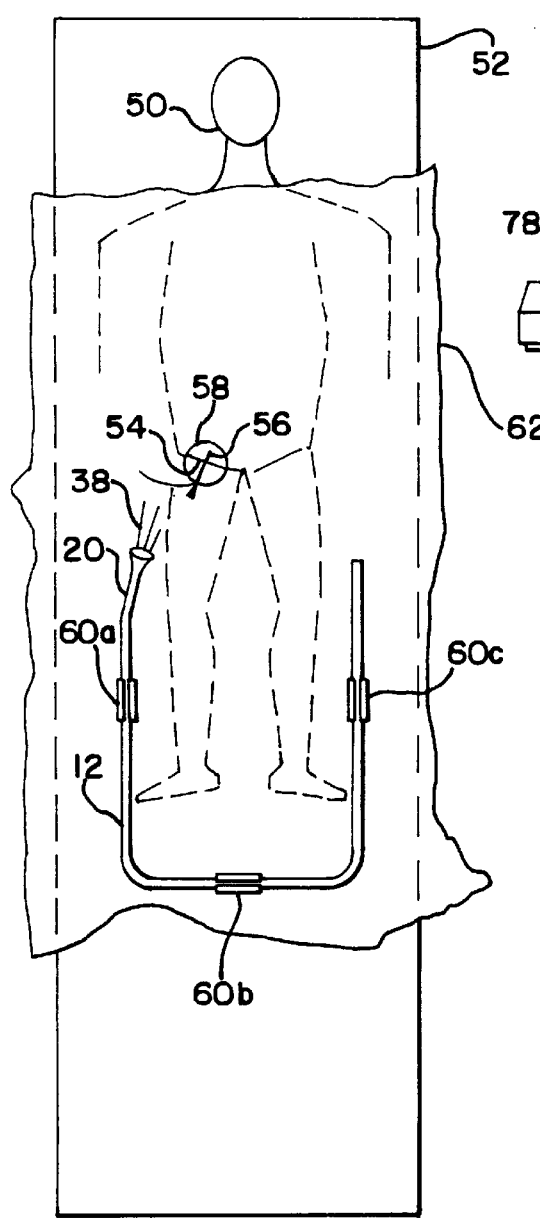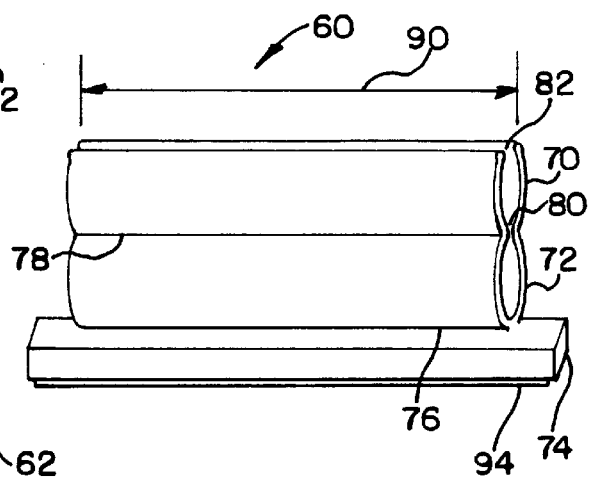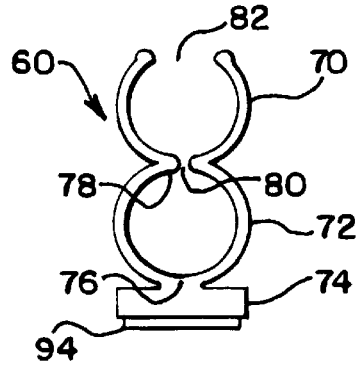

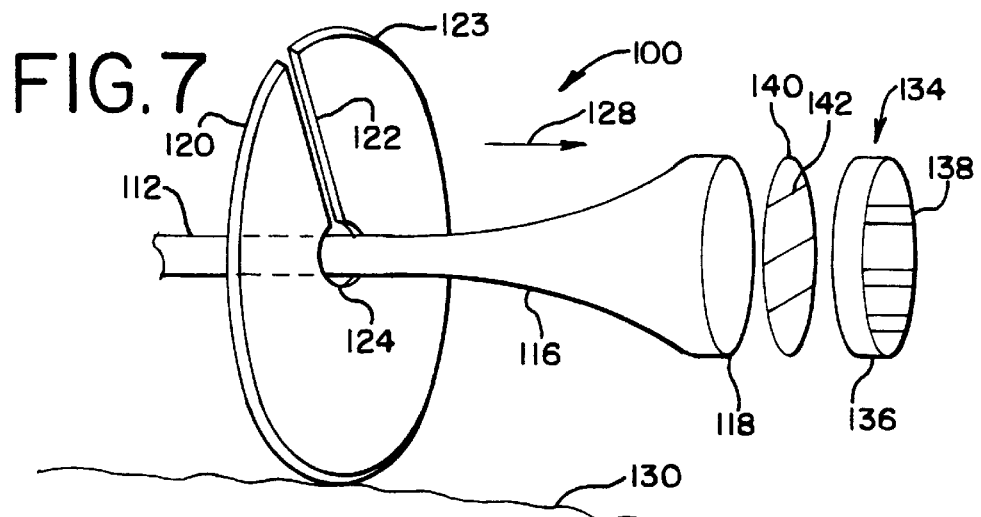
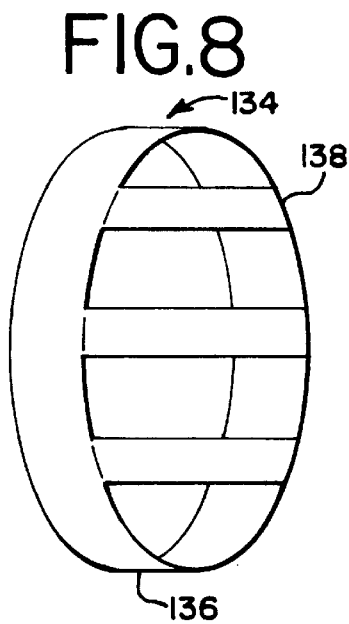
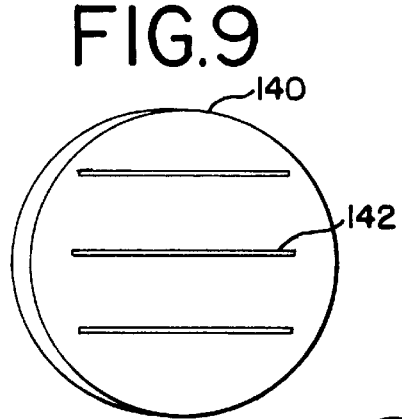
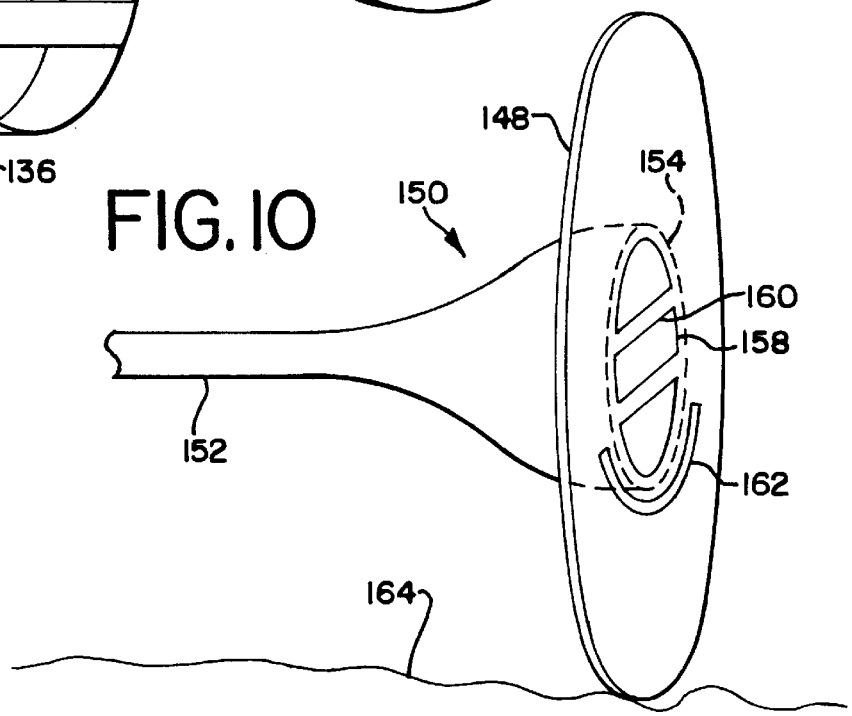

METHOD AND APPARATUS FOR STORING MEDICAL GUIDEWIRES

BACKGROUND OF THE INVENTION

A number of interventional radiologic medical techniques have been recently developed to address a variety of potentially life-threatening human ailments. For example, interventional radiologic techniques have been developed to allow removal and/or destruction of stones in the biliary or excretory systems, blood clots in blood vessels and foreign bodies introduced by surgery that have migrated or become dysfunctional. As another example, interventional radiologic techniques may be utilized to treat stenosis, a degenerative blood vessel condition that causes a narrowing or constriction of the lumen so that blood flow is restricted. Due to their minimally invasive nature, interventional radiologic techniques provide an attractive alternative to surgery and thus have become very popular.

Interventional radiologic techniques typically utilize a wire that passes from outside of the patient's body, through his or her skin and into the tubular structure of interest. Once the wire is positioned in the desired location, medical devices, such as catheters, may be passed over the wire and thereby guided into the tubular structure so that the desired medical procedure may be performed. These "guidewires", as they have come to be called, are of various lengths, calibers and materials, depending on the use for which they are intended.

In use, guidewires, after removal from their sterile packaging, are inserted into the patient and the portion remaining outside of the patient's body is spooled by hand, as would be an extension cord. More specifically, the external portion of a guidewire is wound about itself in such a way as to "lock" the wire from springing into its naturally straight configuration. The wound portion of the guidewire is then placed into a large bowl containing a sterile saline solution so as to keep the wire wet. The saline solution also promotes the dissolution of any clots which may have formed on the guidewire after it is removed from the patient and placed in the bowl.

Oftentimes several different guidewires may be used during a single procedure. As a result, a number of wound guidewire portions may accumulate in a bowl. In addition, several catheters may be placed in the bowl. It thus often becomes difficult for a physician to locate a specific guidewire within the bowl during a procedure.

Wound guidewires also have a tendency to straighten once unlocked. As a result, a guidewire may spring open unexpectedly when it is being unwound during a procedure. When this occurs, the guidewire may inadvertently come into contact with non-sterile areas of the procedure room, and hence need to be resterilized or completely replaced.

The bowls containing the wound guidewire portions and catheters may also be accidently tipped over during procedures. Such a scenario would also likely result in the catheters and guidewires coming into to contact with non-sterile areas of the procedure room such as the floor.

Accordingly, it is an object of the present invention to provide a method and apparatus for storing medical guidewires that maintains them submersed in liquid.

It is another object of the present invention to provide a method and apparatus for storing multiple medical guidewires of various sizes and types so that they are organized for easy identification and access.

It is another object of the present invention to provide a method and apparatus for storing medical guidewires that allows for their easy introduction into a patient and removal therefrom.

It is still another object of the present invention to provide a method and apparatus for storing medical guidewires so that they don't spring open unexpectedly during a procedure.

It is still another object of the present invention to provide a method and apparatus for storing medical guidewires that prevents their contact with non-sterile portions of the procedure room.

SUMMARY OF THE INVENTION

The present invention is directed to a method and apparatus for storing medical guidewires. The apparatus features a flexible, hollow pipe having a sealed end and an open end. A nozzle is disposed at the open end of the flexible pipe by a friction joint. As a result, the nozzle may be removed or repositioned. The nozzle features an elbow portion so that the opening of the nozzle is elevated above the flexible pipe. Alternatively, the open end of the flexible pipe is elevated by a collar or stand. This allows fluid to be retained in the flexible pipe. The nozzle or open end is flared and features a number of dividers. These dividers support and organize the guidewires that have been placed within the flexible pipe for easy access by the physician. The flexible pipe may contain a wiping plate formed of gauze or the like with slits aligned with the dividers so that the guidewires may be automatically wiped.

The flexible pipe may be secured in a coiled configuration with one or more clamps. Alternatively, the flexible pipe may be uncoiled and attached to a surface, such as the sterile drapes covering a patient, using one or more wire/catheter guides. The wire/catheter guides feature stacked channels positioned upon a base. The base features adhesive so the wire/catheter guide may be attached to the surface of interest. The channels are sized to accommodate the flexible pipe and feature longitudinal grooves or openings. As a result, the flexible pipe may be inserted into one or more of the channels. One possible arrangement is to locate the flexible pipe in one channel while using the other channel to guide catheters or guidewires that are not stored within the flexible pipe.

BRIEF DESCRIPTION OF THE DRAWINGS

FIGS. 1A and 1B are perspective views of an embodiment of the apparatus for storing medical guidewires of the present invention in a coiled configuration without and with medical guidewires inserted therein, respectively;

FIG. 2 is an enlarged end elevation view of the clamp of the apparatus of FIGS. 1A and 1B;

FIG. 3 is an enlarged perspective view of the nozzle of the apparatus of FIGS. 1A and 1B;

FIG. 4 is a top plan view of the apparatus of FIGS. 1A and 1B utilizing wire/catheter guides during a medical procedure;

FIG. 5 is an enlarged perspective view of one of the wire/catheter guides of FIG. 4;

FIG. 6 is an end elevation view of the wire/catheter guide of FIG. 5;

FIG. 7 is a partial perspective view of a second embodiment of the apparatus for storing medical guidewires of the present invention;

FIG. 8 is an enlarged perspective view of the divider cap of the apparatus of FIG. 7;

FIG. 9 is an enlarged perspective view of the wiping plate of the apparatus of FIG. 7;

FIG. 10 is a partial perspective view of a third embodiment of the apparatus for storing medical guidewires of the present invention.

DESCRIPTION OF THE PREFERRED EMBODIMENTS

Referring to FIGS. 1A and 1B, an embodiment of the apparatus of the present invention, in a coiled configuration, is indicated generally at 10. The apparatus 10 features a flexible pipe 12 that is sealed on one end 14. The open end 16 is fitted with a nozzle 20. A number of clamps 22 are attached to flexible pipe 12 so as to hold it in the coiled configuration. Flexible pipe 12, clamps 22 and nozzle 20 are preferably made of flexible polymeric plastic. While the embodiment shown in FIGS. 1A and 1B shows the nozzle 20 as a separate piece that is attached to flexible pipe 12, it is to be understood that the flexible pipe and nozzle could be manufactured as a single, integral piece.

As shown in FIG. 2, clamp 22 features a number of interconnected "C-shaped" sections. The inner surface 26 of each C-shaped section defines a generally circular area that is slightly smaller than the cross section defined by the outer surface of flexible pipe 12. As a result, flexible pipe 12 may be inserted into, and secured within, clamp 22. It is to be noted that while three such C-shaped sections are shown in FIG. 2, clamp 22 may incorporate any number of such sections so that the flexible pipe 12 of the device (FIGS. 1A and 1B) may be wound into more or less than three coils.

As shown in FIG. 3, the nozzle 20 of the device preferably features an elbow portion 30 and a flared portion 32. Flared portion 32 features an enlarged opening, the latter of which is spanned by dividers 36. Dividers 36 are essentially strips of plastic that are attached by their ends to the interior of the flared portion 32 of nozzle 20. The enlarged opening and dividers 36 allow a multitude of guidewires 38 to be inserted into the device while keeping them separated and organized, as illustrated in FIG. 1B. As a result, the physician is better able to select the proper guidewire during a procedure. It is to be noted that the configuration of the dividers 36 shown is an example only. The dividers or grating across the opening could take on a number of configurations including, for example, a crossed arrangement.

Elbow portion 30 maintains flared portion 32 in an elevated state so that liquid, such as sterile saline solution, may be retained within flexible pipe 12. This allows the guidewires 38 to remain primarily submersed in the fluid.

Nozzle 20 is preferably attached to an end of flexible pipe 12 via a friction joint 40. More specifically, the cross-sectional area defined by the inner surface of the non-flared portion of nozzle 20 is slightly smaller than the cross-sectional area defined by the outer surface of flexible pipe 12. As a result, nozzle 20 and flexible pipe 12 are joined in an interference-fit fashion so that liquid will not leak out. In addition, friction joint 40 allows nozzle 30 to be rotated about flexible pipe 12 through 360°, as illustrated by arrow 42, to allow for adjustment and positioning of flexible pipe 12 without the removal of the liquid or guidewires therein. Friction joint 40 also allows nozzle 20 to be removed so that guidewires inadvertently placed beyond the enlarged opening and dividers 36 may be easily retrieved from flexible pipe 12.

As stated previously, clamps 22 (FIGS. 1A and 1B) are easily removable from flexible pipe 12 so that the latter may be straightened or placed in a more convenient configuration. For example, the flexible pipe 12 may be placed in a configuration roughly outlining a patient 50 laying on a procedure table 52, as illustrated in FIG. 4. As shown in FIG. 4, the flexible pipe 12 is held in place on the sterile drapes 62 covering the patient 50 by way of wire/catheter guides 60a, 60b and 60c. With flexible pipe 12 so positioned, the physician may select the guidewires 38 to be inserted into the patient through access site 54.

Access site 54 is an incision in the patient's skin that leads to the tubular structure of interest within the patient's body. As is known in the art, a sheath 56 is inserted through the site 54 so that guidewires 38 may be introduced into the tubular structure. An opening 58 in sterile drape 62 allows the physician to access sheath 56.

When in an uncoiled arrangement, such as the one illustrated in FIG. 4, the flexible pipe 12 offers less resistance to the movement of the guidewires 38 stored therein. As a result, the physician may more easily withdraw guidewires 38 from flexible pipe 12, and feed guidewires 38 into flexible pipe 12, during a procedure. Oftentimes the withdrawal and feeding of guidewires 38 may even be accomplished by a physician using just one hand. This leaves the physician's other hand free for use during more complicated procedures.

Referring to FIGS. 5 and 6, each wire/catheter guide 60 features an upper channel 70 and a lower channel 72 positioned upon a base 74. However, wire/catheter guide 60 may be constructed with any number of channels, including only one. The lower channel 72 is attached by its bottom surface 76 to base 74. The junction 78 between lower channel 72 and upper channel 70 features a longitudinal groove 80 while the upper channel 70 features a longitudinal opening 82.

Wire/catheter guide 60 is preferably constructed of flexible polymeric plastic and upper and lower channels 70 and 72 are sized so that flexible pipe 12 (FIG. 4) may be held snugly therein while still permitting some movement. The lengths of channels 70 and 72, indicated at 90 in FIG. 5, is preferably between 1 and 6 cm. Opening 82 is sized so that flexible pipe 12 may be snapped therethrough and into upper channel 70. Similarly, groove 80 allows flexible pipe 12 to be pressed therethrough and into lower channel 72.

By providing a pair of channels 70 and 72, wire/catheter guide 60 may accommodate two flexible pipes 12. Furthermore, it is possible to use one of the channels 70 or 72 to accommodate flexible pipe 12 while the other is used to guide catheters or guidewires that are not stored within flexible pipe 12. The wire/catheter guide 60 may also be used independently of flexible pipe 12 to guide catheters and guidewires.

The bottom 92 of base 74 features an adhesive 94. As a result, the wire/catheter guide may be positioned in a number of locations including, for example, on the sterile drapes covering the patient (as shown in FIG. 4) or on the procedure table itself.

A second embodiment of the apparatus of the present invention is indicated generally at 100 in FIG. 7. Like the embodiment of FIGS. 1A and 1B, apparatus 100 features a flexible pipe 112 with a sealed end (not shown). In contrast to the embodiment of FIGS. 1A and 1B, however, apparatus 100 does not feature a nozzle that is separable from the flexible pipe 112. Flexible pipe 112 features a flared portion 116 that terminates into, or is adjacent to, open end 118.

An elevating collar 120, preferably formed of thin plastic, features a radial groove 122 extending from the edge 123 of the collar to a central aperture 124. As a result, flexible pipe 112 may be passed through radial groove 122 so that the flexible pipe is positioned through central aperture 124 (as shown in FIG. 7). Elevating collar may then be slid in the direction of arrow 128 until central aperture 124 grips the surface of flared portion 116. When so positioned, elevating collar 120 operates to maintain open end 118 in an elevated position with respect to the remaining portion of flexible pipe 112 and a surface 130. As a result, liquid, such as sterile saline solution, may be retained within flexible pipe 112. It should be noted that elevating collar 120 may feature a shape other than that of a disk.

A divider cap, indicated generally at 134, is sized so as to removably engage flexible pipe 112 so as to cover open end 118. As shown in FIGS. 7 and 8, divider cap 134 features a rim 136 across which a number of dividers 138 are positioned. Dividers 138 are essentially thin strips of material formed across rim 136. When placed over open end 118, the dividers 138 are capable of supporting a number of guidewires in a spaced and organized fashion for easy access by the physician. Divider cap 134 is preferably made from plastic. It should be noted that the configuration shown for dividers 138 is an example only and that a variety of other grating arrangements (such as crossed dividers) are possible.

A wiping plate, indicated at 140 in FIGS. 7 and 9, is sized so that it may be positioned within flexible pipe 112, just barely inside open end 118. Wiping plate 140 is preferably made of gauze or a similar material such as TEFLA. Wiping plate 140 is provided with a number of slits 142 positioned so as to be aligned with the top edges of dividers 138 (or whatever divider configuration is utilized). The inclusion of wiping plate 140 allows guidewires to be automatically wiped upon introduction into and withdrawal from flexible pipe 112. Divider cap 134 may be removed from flexible pipe 112 to allow removal or insertion of wiping plate 140.

The separate divider cap 134 and elevating collar 120 of FIG. 7 may be replaced by a single multifunction stand 148 as exemplified by the third embodiment of the apparatus, indicated generally at 150 in FIG. 10. As shown in FIG. 10, flexible pipe 152 is virtually identical to the flexible pipe 112 of FIG. 7 except that it features a circumferential lip 154 surrounding open end 158.

A multifunction stand 148 is preferably formed of plastic and is cut to provide a number of dividers 160. In addition, a semi-circular notch 162 is cut out of stand 148. Notch 162 is sized so that lip 154 may be received so that stand 148 is attached to flexible pipe 152. As a result, open end 158 is elevated above surface 164 so that liquid may be contained within flexible pipe 152. In addition, guidewires may be placed upon dividers 160 for easy access by the physician. It should be noted that multifunction stand 148 does not have to feature the shape of a disk.

While the preferred embodiments of the invention have been shown and described, it will be apparent to those skilled in the art that changes and modifications may be made therein without departing from the spirit of the invention, the scope of which is defined by the appended claims.

What is claimed is:

1. An apparatus for storing medical guidewires comprising:
    a) a hollow flexible pipe capable of being turned or coiled, said flexible pipe having a sealed end and an open end and constructed of a liquid-impermeable material so that liquid may be contained therein;
    b) a nozzle positioned at said open end; and
    c) at least one divider strip positioned across at least a portion of said nozzle whereby guidewires may be inserted into and withdrawn from said flexible pipe and organized for easy selection.

2. The apparatus of claim 1 wherein said nozzle includes an elbow portion so that said nozzle may be elevated above said flexible pipe so that fluid may be contained in said flexible pipe.

3. The apparatus of claim 1 wherein said nozzle includes a flared portion.

4. The apparatus of claim 1 wherein said nozzle is joined to said flexible pipe by a friction joint so that said nozzle may be selectively positioned on or removed from said flexible pipe.

5. The apparatus of claim 1 further comprising a clamp featuring a plurality of sections, each section removably receiving a portion of said flexible pipe so that said flexible pipe is arranged in a coiled configuration.

6. The apparatus of claim 1 further comprising a wire/catheter guide, said wire/catheter guide including a channel positioned upon a base, said channel having a longitudinal groove and a portion of said flexible pipe removably received therein.

7. The apparatus of claim 6 wherein said base of said wire/catheter guide includes a bottom featuring an adhesive so that said wire/catheter guide may be secured to a surface.

8. The apparatus of claim 1 wherein said at least one divider is included in a divider cap, said divider cap also including a rim to which said at least one divider is attached, said rim sized to removably engage said nozzle.

9. The apparatus of claim 1 further comprising a wiping plate sized to be inserted within said nozzle, said wiping plate including at least one slit aligned with said at least one divider so that medical guidewires are automatically wiped upon insertion into and removal from said flexible pipe.

10. The apparatus of claim 1 further comprising an elevating collar including a central aperture and a radial groove extending from the central aperture to the edge of the elevating collar, said central aperture sized to receive said flexible pipe after said flexible pipe is slid through said radial groove and said elevating collar sized to elevate said nozzle above a surface.

11. The apparatus of claim 1 wherein said at least one divider is included in a multifunction stand, said multifunction stand also including a notch sized so as to receive a lip formed upon said nozzle and said multifunction stand sized to elevate said nozzle above a surface.

12. An apparatus for storing medical guidewires comprising:
    a) a hollow flexible pipe capable of being turned or coiled, said flexible pipe having a sealed end and an open end and constructed of a liquid-impermeable material so that liquid may be contained therein; and
    b) at least one divider strip positioned across at least a portion of said open end whereby guidewires may be inserted into or withdrawn from said flexible pipe and organized for easy selection.

13. The apparatus of claim 12 wherein said hollow flexible pipe includes a flared portion adjacent said open end.

14. The apparatus of claim 12 further comprising a clamp featuring a plurality of sections, each section removably receiving a portion of said flexible pipe so that said flexible pipe is arranged in a coiled configuration.

15. The apparatus of claim 12 further comprising a wire/catheter guide, said wire/catheter guide including a channel positioned upon a base, said channel having a longitudinal groove and a portion of said flexible pipe removably received therein.

16. The apparatus of claim 15 wherein said base of said wire/catheter guide includes a bottom featuring an adhesive so that said wire/catheter guide may be secured to a surface.

17. The apparatus of claim 12 wherein said at least one divider is included in a divider cap, said divider cap also including a rim to which said at least one divider is attached, said rim sized to removably engage the open end of said flexible pipe.

18. The apparatus of claim 12 further comprising a wiping plate sized to be inserted within said flexible pipe, said wiping plate including at least one slit aligned with said at least one divider so that medical guidewires are automatically wiped upon insertion into and removal from said flexible pipe.

19. The apparatus of claim 12 further comprising an elevating collar including a central aperture and a radial groove extending from the central aperture to the edge of the elevating collar, said central aperture sized to receive said flexible pipe after said flexible pipe is slid through said radial groove and said elevating collar sized to elevate said open end above a surface.

20. The apparatus of claim 12 wherein said at least one divider is included in a multifunction stand, said multifunction stand also including a notch sized so as to receive a lip formed upon the open end of said flexible pipe and said multifunction stand sized to elevate the open end above a surface.

* * * * *